United States Patent
Holbery et al.

(10) Patent No.: US 9,911,559 B2
(45) Date of Patent: Mar. 6, 2018

(54) MAGNETICALLY ALIGNED CIRCUIT

(71) Applicant: Microsoft Technology Licensing, LLC, Redmond, WA (US)

(72) Inventors: James David Holbery, Bellevue, WA (US); Andrew L. Fassler, Pittsburgh, PA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 0 days.

(21) Appl. No.: 15/011,248

(22) Filed: Jan. 29, 2016

(65) Prior Publication Data

US 2017/0221660 A1    Aug. 3, 2017

(51) Int. Cl.
| | |
|---|---|
| H01H 36/00 | (2006.01) |
| H01H 11/04 | (2006.01) |
| H01H 35/24 | (2006.01) |
| A61N 1/00 | (2006.01) |
| G06F 3/045 | (2006.01) |

(52) U.S. Cl.
CPC .............. *H01H 36/00* (2013.01); *A61N 1/00* (2013.01); *H01H 11/048* (2013.01); *H01H 35/245* (2013.01); *G06F 3/045* (2013.01); *H05K 2201/0379* (2013.01); *H05K 2201/10053* (2013.01); *H05K 2203/104* (2013.01)

(58) Field of Classification Search
CPC ................................. H03K 17/97; G06F 1/163
USPC ..................................... 338/47; 335/205–207
See application file for complete search history.

(56) References Cited

U.S. PATENT DOCUMENTS

| | | | | |
|---|---|---|---|---|
| 3,681,723 A | * | 8/1972 | Goll | H01H 13/702 |
| | | | | 200/517 |
| 3,882,442 A | * | 5/1975 | Hubbard | B60T 7/04 |
| | | | | 303/15 |
| 4,448,837 A | | 5/1984 | Ikeda et al. | |
| 4,548,862 A | | 10/1985 | Hartman | |
| 4,644,101 A | * | 2/1987 | Jin | G06F 3/045 |
| | | | | 178/18.05 |
| 6,011,307 A | | 1/2000 | Jiang et al. | |

(Continued)

FOREIGN PATENT DOCUMENTS

| | | |
|---|---|---|
| EP | 0228829 A2 | 7/1987 |
| WO | 2015117125 A1 | 8/2015 |

OTHER PUBLICATIONS

Yao. et al., "Wearable Multifunctional Sensors using Printed Stretchable Conductors made of Silver Nanowires", In Journal of Nanoscale, vol. 6, Issue 4, Dec. 5, 2013, pp. 2345-2352.

(Continued)

*Primary Examiner* — Alexander Talpalatski
(74) *Attorney, Agent, or Firm* — Alleman Hall Creasman & Tuttle LLP

(57) ABSTRACT

Examples are disclosed that relate to magnetically aligned switching circuits. One disclosed example provides an electronic component comprising a first terminal, a second terminal, and a deformable host material arranged between the first terminal and the second terminal. Aligned magnetically within the host material is an ensemble of particles each comprising a ferromagnetic material, each particle having greater electrical conductivity than the host material. The ensemble of particles is configured to form at least one complete conduction path from the first terminal to the second terminal.

15 Claims, 10 Drawing Sheets

(56) References Cited

U.S. PATENT DOCUMENTS

| | | | |
|---|---|---|---|
| 6,274,832 B1* | 8/2001 | Tachibana | H01H 21/24 200/343 |
| 6,392,527 B1* | 5/2002 | Gilano | B60R 21/0132 280/735 |
| 8,587,493 B2 | 11/2013 | Dickey et al. | |
| 9,581,972 B1* | 2/2017 | Arrow | H02J 7/0044 |
| 9,609,921 B1* | 4/2017 | Feinstein | A44C 5/2071 |
| 2003/0205450 A1* | 11/2003 | Divigalpitiya | H01H 1/029 200/512 |
| 2008/0143906 A1 | 6/2008 | Allemand et al. | |
| 2011/0279409 A1 | 11/2011 | Salaverry et al. | |
| 2013/0101755 A1 | 4/2013 | Lee et al. | |
| 2013/0320467 A1 | 12/2013 | Buchanan et al. | |
| 2015/0185764 A1* | 7/2015 | Magi | G06F 1/163 361/679.03 |
| 2015/0309563 A1* | 10/2015 | Connor | G06F 3/011 73/865.4 |

OTHER PUBLICATIONS

Xu, et al., "Highly Conductive and Stretchable Silver Nanowire Conductors", In Journal of Advanced Materials, vol. 24, Issue 37, Sep. 25, 2012, 9 pages.

Xu, Feng, "Applications of One-Dimensional Nanomaterials for Stretchable Electronics", In Doctoral Dissertation of North Carolina State University, Retrieved on: Nov. 4, 2015, 160 pages.

Chen, et al., "Annealing-Free Solution-Processed Silver NanowirePolymer Composite Transparent Electrodes and Flexible Device Applications", In Proceedings of IEEE Transactions on Nanotechnology, vol. 14, Issue 1, Oct. 13, 2014, 10 pages.

Tevis, et al., "Synthesis of Liquid Core-Shell Particles and Solid Patchy Multicomponent Particles by Shearing Liquids Into Complex Particles (SLICE)", In Journal of Langmuir, vol. 30, Issue 47, Dec. 2, 2014, pp. 14308-14313.

Gu, et al., "Transparent Elastic Capacitive Pressure Sensors based on Silver Nanowire Electrodes", In Proceedings of 8th IEEE International Conference on Nano/Micro Engineered and Molecular Systems, Apr. 7, 2013, pp. 1183-1185.

Chung, et al., "Solution-Processed Flexible Transparent Conductors Composed of Silver Nanowire Networks Embedded in Indium Tin Oxide Nanoparticle Matrices", In Journal of Nano Research, vol. 5, Issue 11, Nov. 2012, 10 pages.

Oh, et al., "Silver Nanowire Transparent Conductive Electrodes for High-Efficiency III-Nitride Light-Emitting Diodes ", Journal Scientific Reports, Sep. 3, 2015, 45 pages.

Akter, T. et al., "Reversibly Stretchable Transparent Conductive Coatings of Spray-Deposited Silver Nanowires," ACS Applied Materials and Interfaces, vol. 4, No. 4, Apr. 3, 2012, 5 pages.

Kim, B. et al., "Interfacing Liquid Metals with Stretchable Metal Conductors," ACS Applied Materials and Interfaces, vol. 7, No. 15, Apr. 2, 2015, 7 pages.

Martinez, V. et al., "Stretchable Silver Nanowire-Elastomer Composite Microelectrodes with Tailored Electrical Properties," ACS Applied Materials and Interfaces, vol. 7, No. 24, Jun. 11, 2015, 9 pages.

ISA European Patent Office, International Search Report and Written Opinion Issued in PCT Application No. PCT/US2017/013633, Apr. 26, 2017, WIPO, 13 Pages.

* cited by examiner

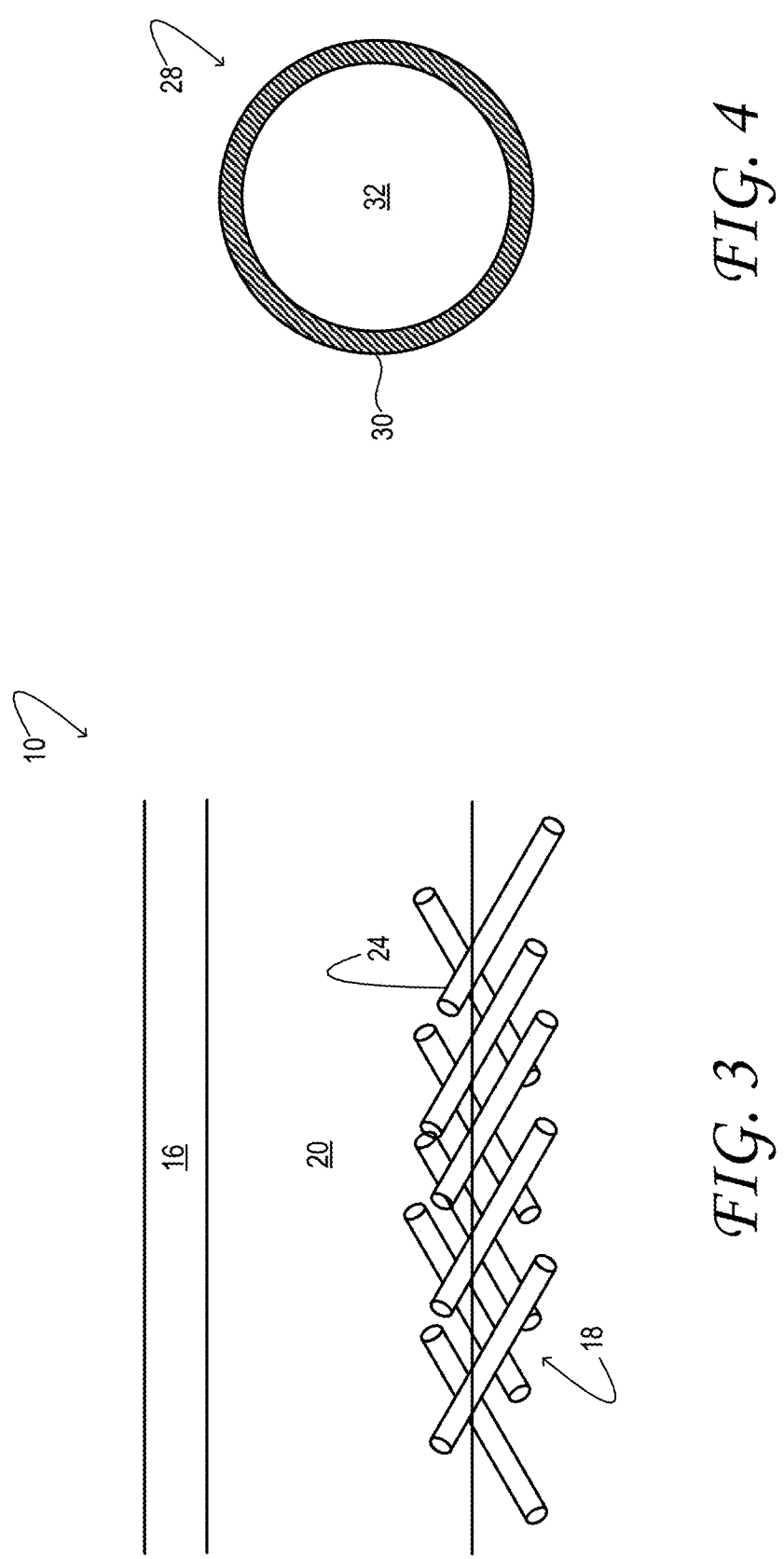

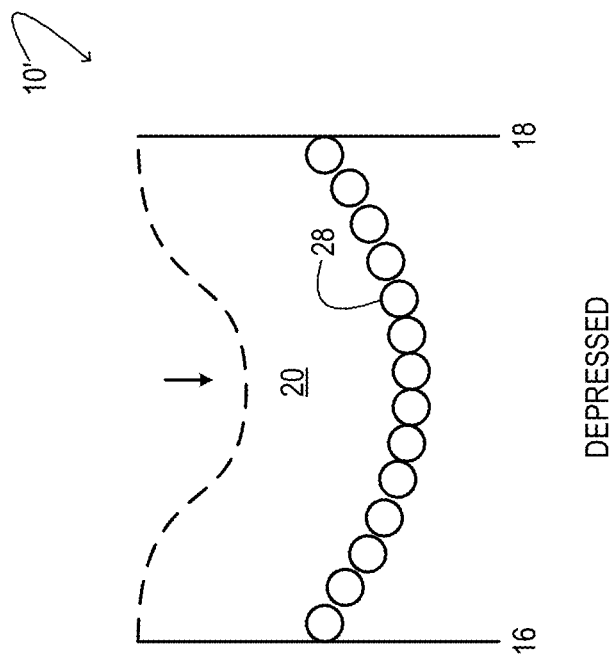
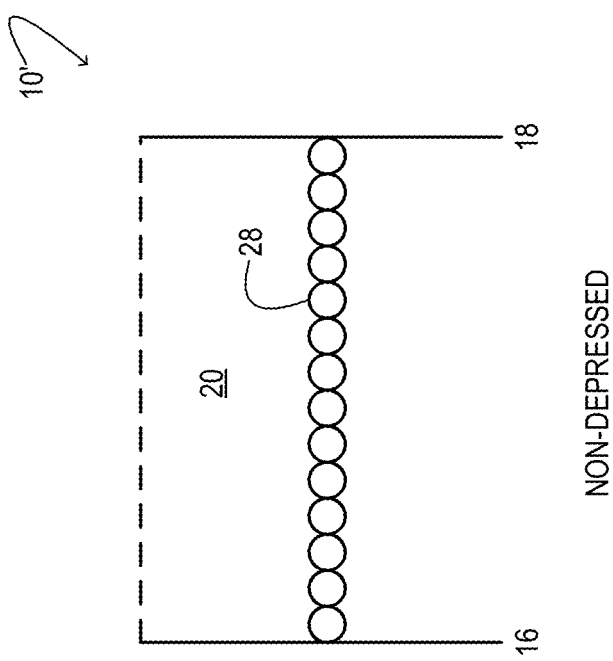
FIG. 5B

MAGNETICALLY ALIGNED CIRCUIT

BACKGROUND

An electronic device may be configured to interface with a human being in various ways. Some electronic devices may include one or more mechanical switches, which the user actuates via touch pressure. Other devices use resistive or capacitive touch sensing, or non-contact approaches to receive user input. Still other devices may include one or more electrodes coupled electrically to the user's skin.

SUMMARY

Examples are disclosed that relate to magnetically aligned switching circuits. One disclosed example provides an electronic component comprising a first terminal, a second terminal, and a deformable host material arranged between the first terminal and the second terminal. Aligned magnetically within the host material is an ensemble of particles each comprising a ferromagnetic material, each particle having greater electrical conductivity than the host material. The ensemble of particles is configured to form at least one complete conduction path from the first terminal to the second terminal.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve the disadvantages identified in this disclosure.

BRIEF DESCRIPTION OF THE DRAWINGS

FIG. 3 shows aspects of an example second terminal of an electronic component of a wearable electronic device.

FIG. 4 shows aspects of an example particle of an ensemble of aligned particles in an example electronic component.

FIGS. 5A and 5B show aspects of example scenarios in which conduction through a host material of an electronic device changes with oriented depression of the host material.

DETAILED DESCRIPTION

Figure 1:
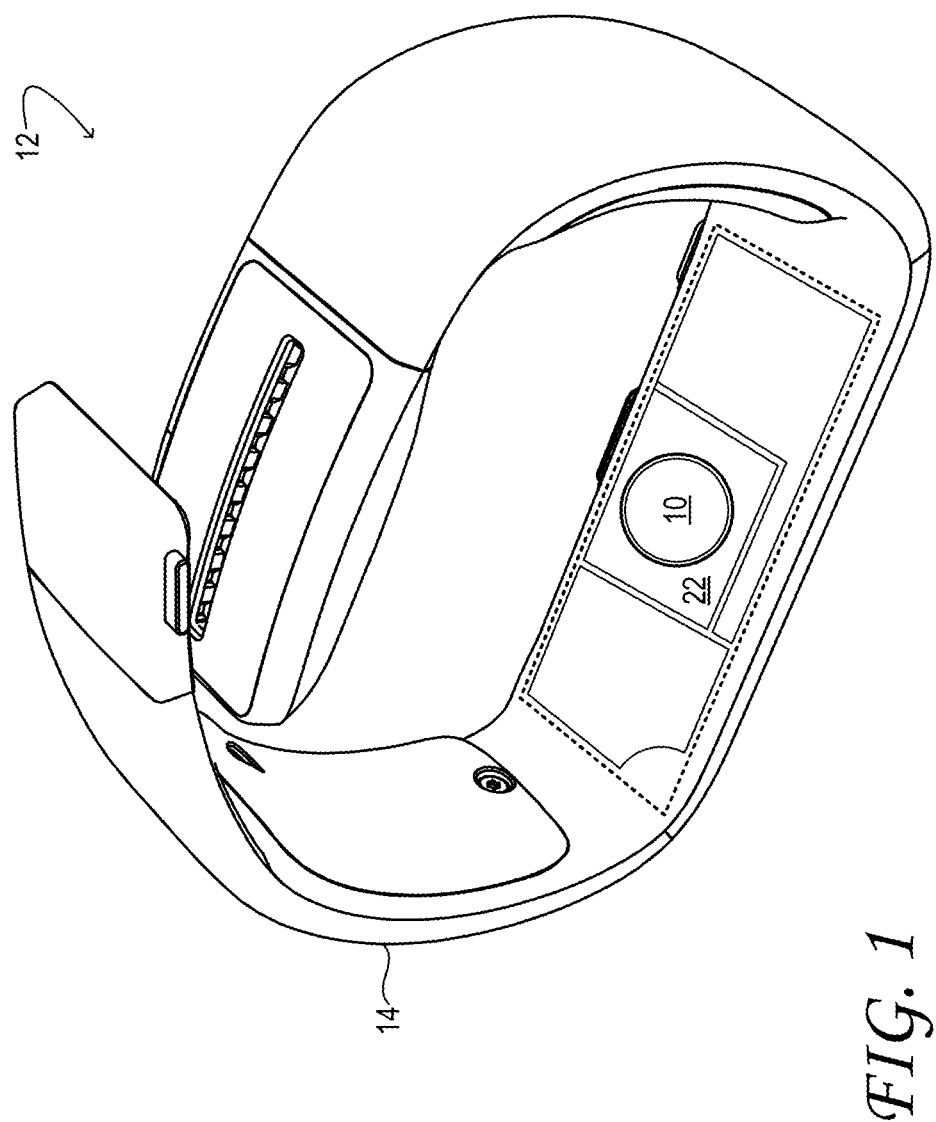
FIG. 1 shows aspects of an example wearable electronic device.

The examples disclosed herein relate to flexible electronic componentry, including flexible, pressure-sensitive electrical switches and electrodes to be worn on the human body. The disclosed examples utilize a thin layer of deformable, host material and an ensemble of magnetically aligned conductive particles embedded therein. Under appropriate conditions, the particles form a complete conduction path through the host material, between terminals arranged on opposite sides of the host material. In wearable implementations, one of the terminals can be configured to make an electrical contact to living human skin. The opposite terminal may be configured for resilient flexibility, so that the electronic component can be worn and used on a flexible body part. In some implementations, a complete conduction path through the ensemble of particles is formed upon depression of the host material through the flexible terminal, and is broken when the depression is released. This type of component can be used as a momentary electrical switch, as one example implementation.

Aspects of this disclosure will now be described by example and with reference to the drawing figures listed above. Components, process steps, and other elements that may be substantially the same in one or more of the figures are identified coordinately and are described with minimal repetition. It will be noted, however, that elements identified coordinately may also differ to some degree. It will be further noted that the figures are schematic and generally not drawn to scale. Rather, the various drawing scales, aspect ratios, and numbers of components shown in the figures may be purposely distorted to make certain features or relationships easier to see.

FIG. 1 shows one view of an example electronic component 10 of a wearable electronic device 12. Electronic component 10 is an electrode intended to contact the living human skin of the device wearer. In some implementations, the electronic component may be five to ten millimeters in diameter. In other implementations, the electronic component may be larger or smaller, and may have any desired shape. In FIG. 1, electronic component 10 is held against the wearer's skin by flexible band 14 of electronic device 12. In other implementations, replaceable adhesive pads or tape may be used to secure the electronic component to the wearer's skin. The pads or tape may include a pressure-activated, hypoallergenic adhesive that yields to lift-off force.

Figure 2:
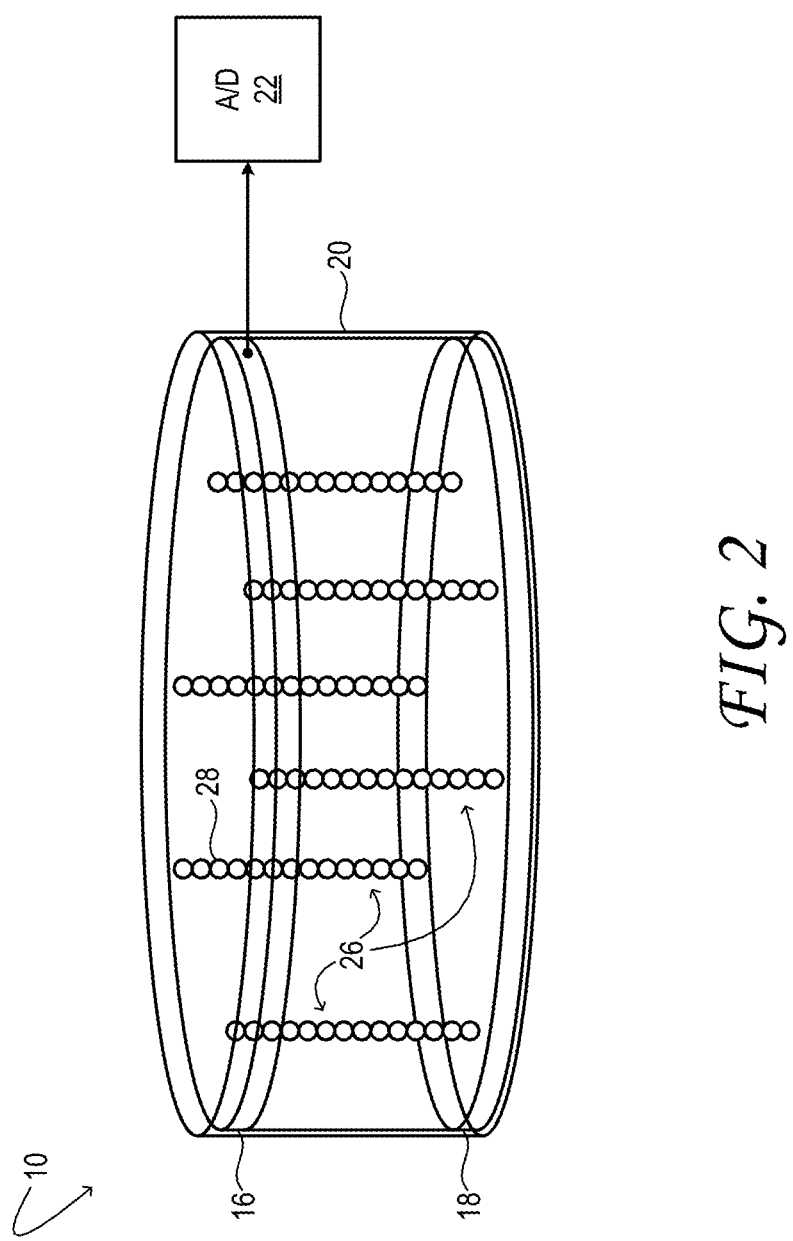
FIG. 2 shows aspects of an example electronic component of a wearable electronic device.

FIG. 2 provides another view of electronic component 10. The electronic component includes a first terminal 16, a second terminal 18, and a thin layer of deformable host material 20 arranged between the first and second terminals. The host material may be stretchable, bendable, and/or depressible. In some implementations, the host material is an electrical insulator. Further, in some implementations, the host material may comprise a soft, thermosetting, elastomeric polymer, such as silicone. Soft rubbers and thermoplastic materials are equally envisaged.

First terminal 16 and second terminal 18 each comprise one or more conductive materials, but are otherwise not particularly limited, either in form or in composition. In some implementations, the first and second terminals may be metallic. In other implementations, the first and second terminals may be formed from a conducting composite material, such as a graphite polymer composite. In some implementations, the first and second conductors may be nominally flat or plate-like. Curved terminals are also envisaged.

First terminal 16 provides electronic conduction through the interior of host material 20. In FIG. 2, the first terminal is coupled electrically to analog-to-digital (A/D) convertor 22 of wearable electronic device 12. This configuration enables various forms of electrical monitoring of the wearer's physiology, including galvanic skin-resistance monitoring and electrocardio- or electroencephalographic monitoring, for example. More generally, the electrical monitoring may include detection and/or measurement of any electric current, voltage, or charge from the wearer's body. In some implementations, a wire electrically coupled to the first terminal may be used to conduct current or charge from the wearer's body to a remote monitoring device.

In some implementations, first terminal 16 may be resiliently deformable—e.g., to enable electronic component 10 to be worn over a flexible body part. The first terminal may comprise eutectic gallium indium (EGaIn), for example. With a conductivity of $3.4 \times 10^6$ siemens per meter (S/m) and a melting point of 15.5° C., EGaIn is a liquid conductor at room temperature and at human skin and body temperature. An EGaIn first terminal will conform to its container (the deformable host material) at these temperatures, thereby maintaining the flexibility of the host material. The thickness of the first electrode may be one millimeter or less, in some implementations. In other implementations, the first electrode may have any other suitable thickness. To lessen the risk of detachment, damage to, or corrosion of the first terminal, the first terminal may be fully encapsulated and contained by the host material.

Second terminal 18 provides conductivity over a continuous area of a surface of host material 20 (the lower surface in FIG. 2). In skin-wearable implementations, the second terminal may be configured to form an electrical contact to living human skin. Hair follicles and dead outer layers of human skin are liable to be dry and resistive. Accordingly, some skin-contact technologiesuse one or more fine, macroscopic needles to penetrate the resistive outer layer of skin and access moister, living tissue. Naturally, however, this approach may irritate the wearer's skin. In lieu of macroscopic needles, and referring now to FIG. 3, second terminal 18 of electronic component 10 may include a large number of microscopic filaments 24. The microscopic filaments of the second terminal may be stuck in (e.g. immobilized by and/or adhered to) the surface host material 20 which is opposite first terminal 16. In FIG. 3, microscopic filaments 24 are embedded directly in host material 20; in other implementations, a conductive interface layer may be provided to couple the host material to the microscopic filaments of the second terminal.

In some implementations, microscopic filaments 24 of second terminal 18 may take the form of conductive nanowires—e.g., silver (Ag) or other metal nanowires and/or nanowires of a semiconductor or semi-metal, such as carbon. Nanowires useful for this purpose may be single- or multi-walled, and have any suitable dimensions. Example Ag nanowires may have a diameter of 90±20 nanometers (nm) and a length of up to 30 microns (μm). In other examples, Ag nanowires for filamentous second terminal 18 may have other suitable dimensions. In some implementations, the nanowires or other microscopic filaments of the second terminal may be randomly oriented. In other implementations, the nanowires may be oriented in specific direction and/or angle relative to the surface being contacted.

Returning now to FIG. 2, aligned within host material 20 is an ensemble 26 of particles 28, each particle having greater electrical conductivity than the host material. In some examples, the host material is an electrical insulator (e.g., having a bulk conductivity of $10^{-6}$ S/m or less in some examples), and each particle is a conductor (e.g., having a bulk conductivity of $10^3$ S/m or more in some examples). Accordingly, the ratio of the bulk electrical conductivity of the particles to that of the host material may be $10^9$ or greater in some examples. The ensemble of particles may be configured to form, at least under some conditions, at least one complete conduction path from first terminal 16 to second terminal 18. To that end, each particle 28 may include a highly conductive and a corrosion-resistant outer surface 30, as shown in FIG. 4. Moreover, at least some of the particles may be in contact with each other, at least under some conditions. To facilitate alignment of the particles, each particle may include a ferromagnetic core material 32. As a non-limiting example, the ensemble of particles may include one or more of Ag-coated nickel and Ag-coated ferromagnetic oxide particles. The particles may have any suitable size, and may vary in size between implementations. In implementations in which the host material is arranged in a layer of about 100 microns in thickness, each particle may be about 10 to 50 μm in diameter. For example, Ag coated nickel particles 15 μm in diameter (30% Ag by weight) and/or Ag coated iron oxide 40 μm in diameter (20% Ag by weight) may be used.

The guest-host assembly disclosed herein may provide various advantages over composite materials in which an insulating flexible polymer is loaded with a random dispersion of conductive particles. For example, low-density dispersions may exhibit poor conductivity, because the probability of forming a complete conduction path with low particle densities is low. High-density dispersions may be suitably conductive, but at the expense of various desirable properties of the host polymer, such as flexibility, castability, adhereability, and material hygiene.

Figure 5A:
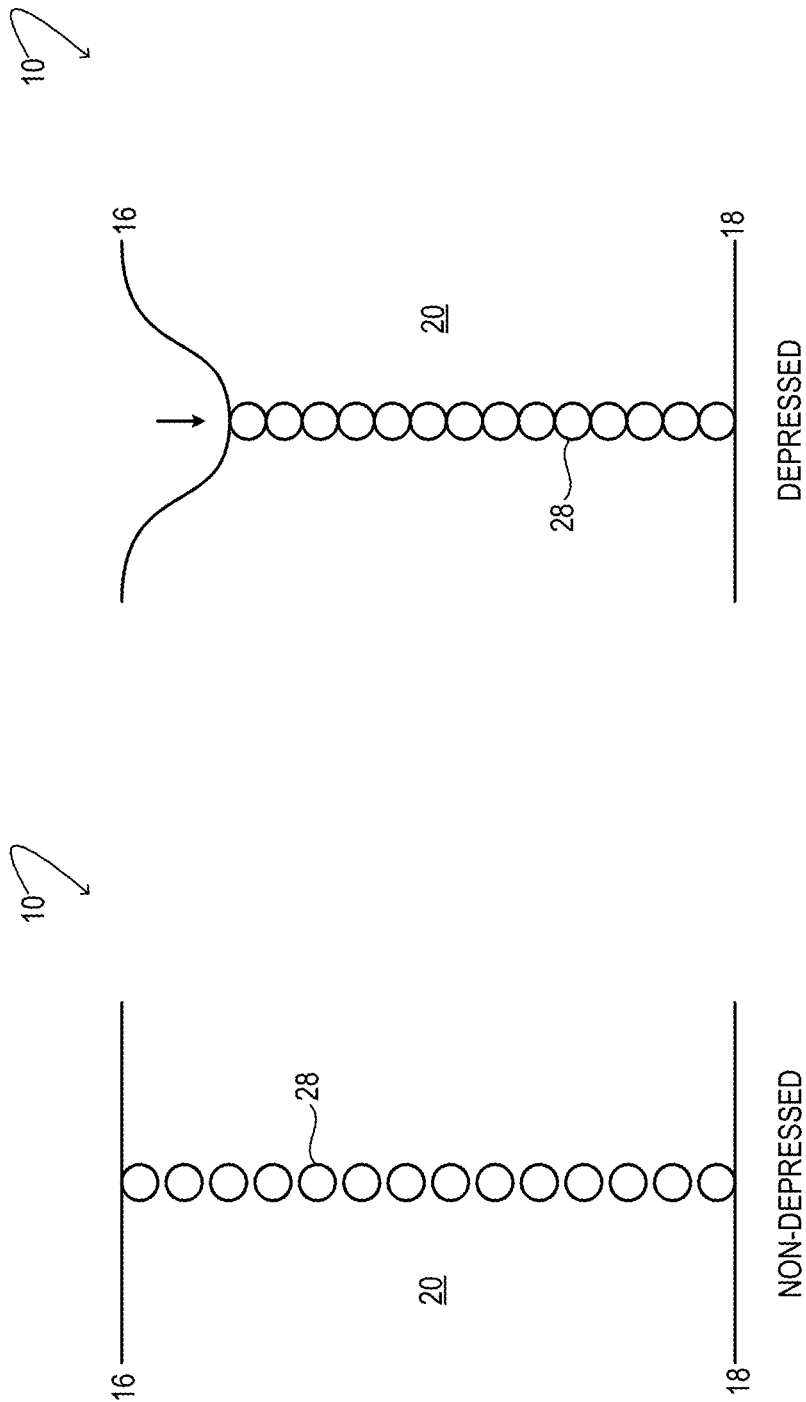

In some implementations, a complete conduction path through the ensemble 26 of particles 28 may not be maintained under all conditions. For instance, the ensemble may form a complete conduction path from first terminal 16 to second terminal 18 only upon oriented depression of host material 20. More specifically, the conduction path may form as a result of initially separated particles moving into contact with each other as the host material is depressed in a direction parallel to the direction of alignment of the ensemble of particles. Depression of the host material may be transmitted readily through first terminal 16, in configurations in which the first terminal itself is deformable. This scenario is shown in FIG. 5A. In some implementations, the host material may remain deformed—and the particles may remain in contact—even after the depression of the host material is released. An electronic component configured in this manner may be used as a pressure-activated electrical contact. In other examples, when the host material is resiliently deformable, the conduction path may be broken upon release of the oriented depression of the host material. Thus, the breaking of the conduction path may result from the particles moving out of contact with each other, as the oriented depression is released. An electronic component configured in this manner may be used as a pressure-sensitive, momentary switch.

Also envisaged is a switching implementation in which conductive particles 28, initially in contact, separate from each other in response to oriented depression of host material 20. The oriented depression in this case may be perpendicular to the direction of alignment of the ensemble of particles, and parallel to the first and second terminals. This scenario is shown in FIG. 5B.

Figure 6:
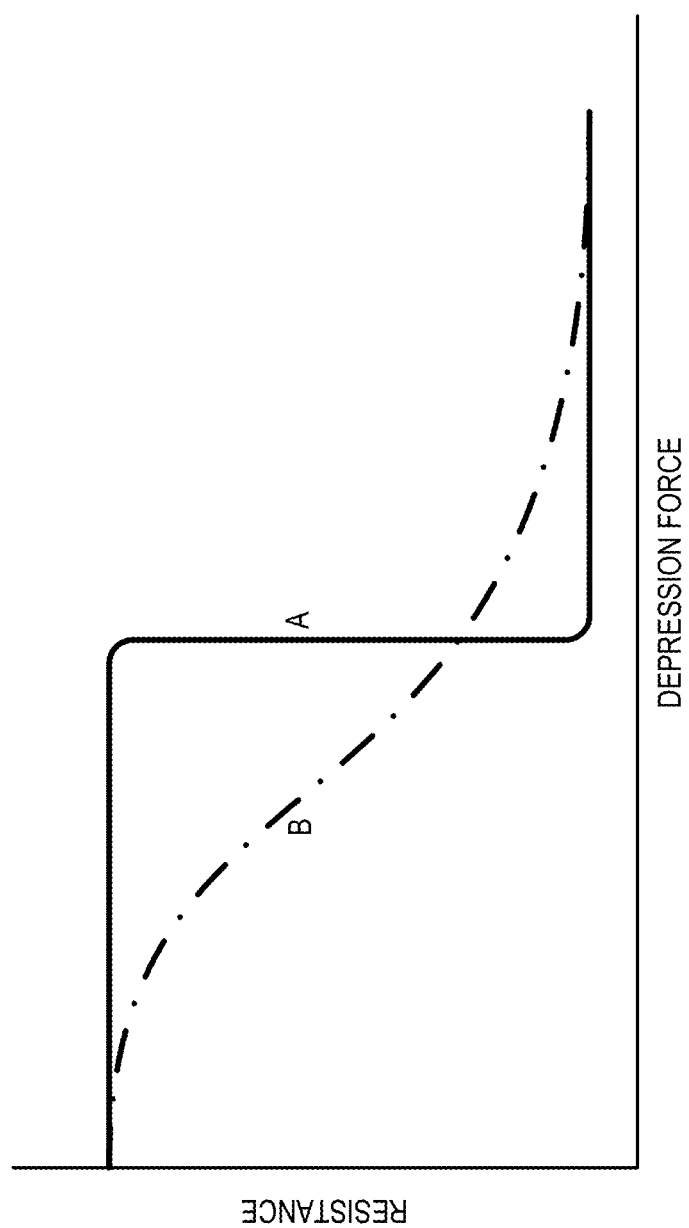
FIG. 6 shows example resistance-versus-depression characteristics of a host material having ensemble of aligned particles.

In the switching implementation shown in FIG. 5A, the electrical resistance of electronic component 10 as measured from first terminal 16 to second terminal 18 may originate at a very high value in the absence of oriented depression, remain at that value through weak oriented depression, and drop abruptly to a low value when at least one complete conduction path through host material 20 is formed. The resulting resistance-versus-depression characteristic is shown in FIG. 6 at A. This behavior may be observed when host material 20 is substantially insulating, and relatively few conduction paths are formed and broken in the host material. In other implementations, when a higher density of conduction paths is available, the resistance drop responsive to depression may be more gradual, as shown at B. In general, the resistance-versus-depression characteristic of electronic component 10 may be tuned by controlling such parameters as the resistivity of the host material, the resistivity of the particles, the bulk loading of the particles in the host material, and the and the detailed geometry of the ensemble 26 of aligned particles (e.g., the area-wise density of columns, the orientation of columns with respect to the depression, etc.).

Figure 7:
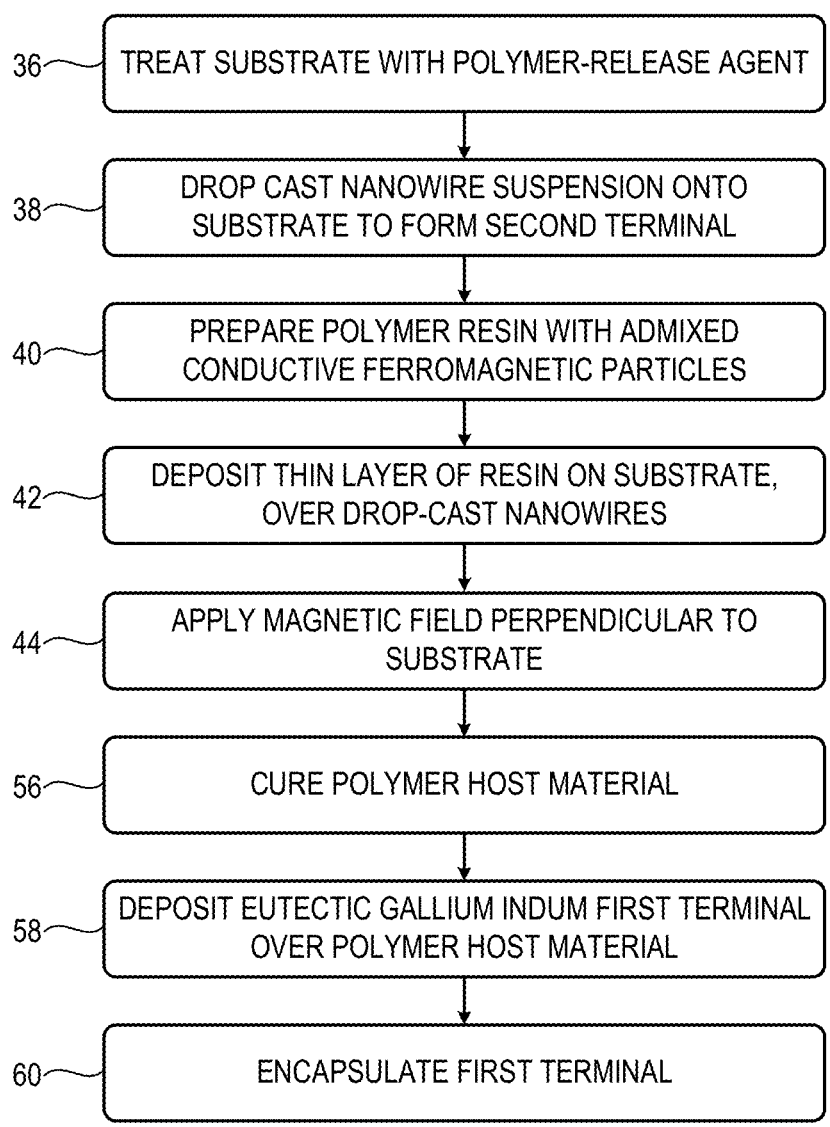
FIG. 7 shows aspects of an example method for fabricating an electronic component of a wearable electronic device.

The manner of incorporating the ensemble 26 of aligned particles 28 in host material 20 is not particularly limited. In some examples, the ensemble of particles may be mixed into the host material in the uncured and/or fluid state, and aligned under the influence of a magnetic field applied during solidification of the host material. In this manner, the particles align along magnetic field lines penetrating the host material. In particular, the magnetic field lines may be arranged between shielded dead zones, in which no particles are aligned. FIG. 7 shows aspects of an example method 34 to fabricate an electronic component 10, of the kind described above.

At 36 of method 34, a substrate (e.g., a mold) is treated with a polymer-release agent to promote facile release of the electronic component 10 from the mold, and to prevent complete encapsulation of the nanowire second terminal (vide infra). Alternatively, a smooth substrate (such as glass or a silicon wafer) can be thoroughly cleaned and left untreated.

At 38 a solvent suspension of microscopic filaments, such as nanowires, is deposited onto the surface of the substrate, and the solvent is allowed to evaporate. For example, an ethanolic suspension of Ag nanowires may be drop-cast onto the substrate. At 40 uncured poly(dimethylsiloxane) (PDMS) resin, or other uncured soft rubber, is prepared, and conductive ferromagnetic particles (such as silver coated nickel or silver coated ferromagnetic oxide) are mixed in. The resin may comprise Sylgard 184 from Dow Corning, and/or various other fluid elastomer resins. Alternatively, the particles may be mixed into a molten thermoplastic, or host material liquefied by incorporation of volatile solvent.

Figure 8:
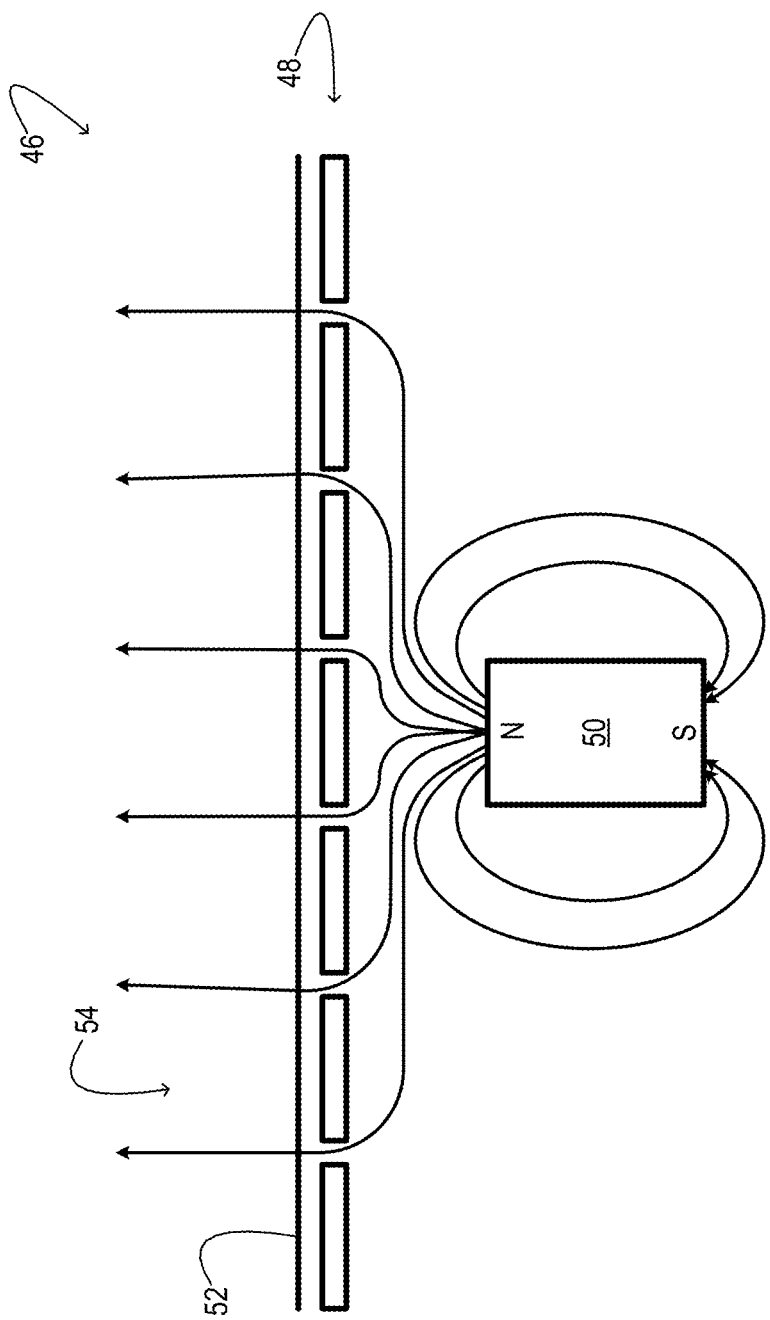
FIG. 8 shows an example polymer curing stage for forming an ensemble of magnetically aligned particles in a polymer host material.

At 42 a thin layer of the above mixture is deposited onto the substrate, over the drop-cast nanowires. This can be achieved using either a bladed applicator or a spin coater. At 44 a magnetic field is applied perpendicular to the substrate, with the field strength decreasing with increasing distance above the substrate. This can be achieved by placing a strong magnet below the substrate. FIG. 8 shows an example polymer curing stage 46 for forming an ensemble of aligned particles in a polymer host material. In some implementations, a patterned, magnetically soft magnetic shield 48 may be positioned between permanent magnet 50 and substrate 52, to provide a plurality of dead zones in which no particles are aligned. In this arrangement, the particles within the polymer host material will align perpendicular to the substrate, spanning the thickness of the polymer host material. In other implementations, the magnetic shield may be omitted, and 'repulsion' among the magnetic field lines may have the effect of aligning the particles along plural, non-intersecting paths through the host material.

Figure 9B:
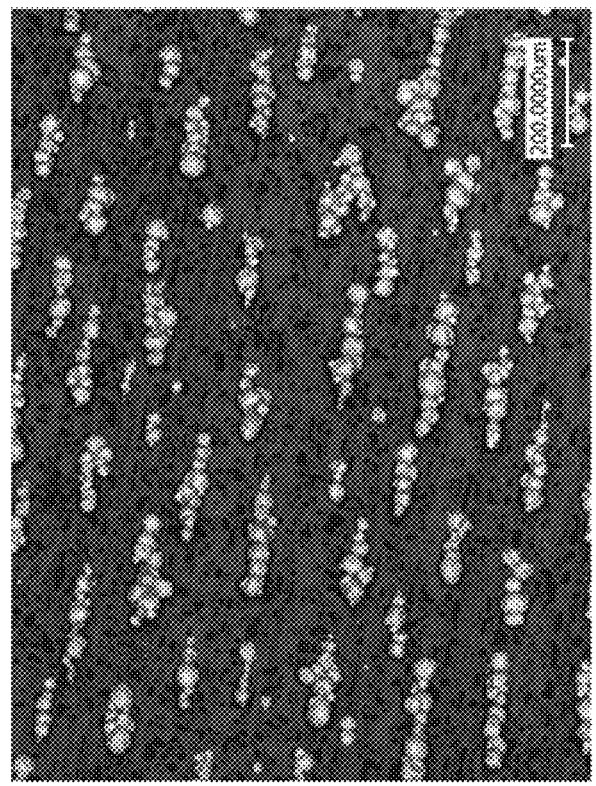
FIGS. 9A and 9B show electron micrographs of an example ensemble of particles aligned magnetically in a host material.
Figure 9A:
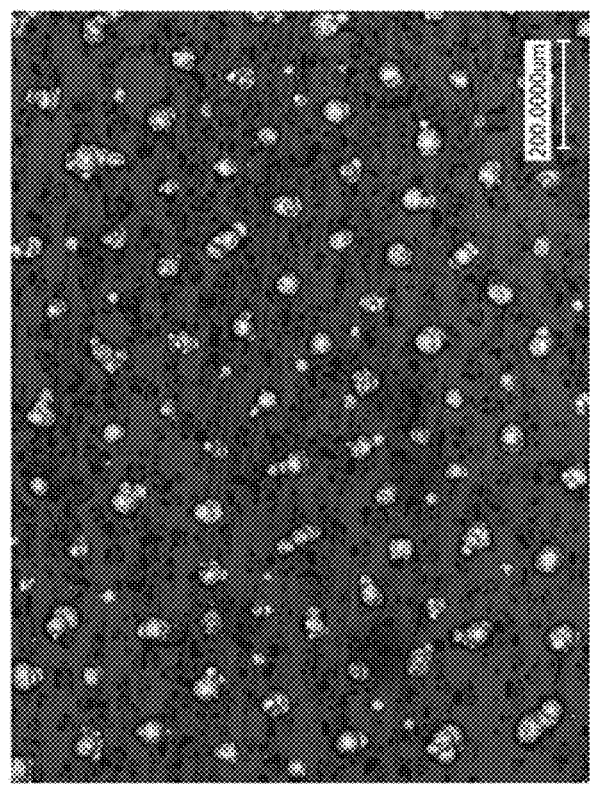

The electron micrographs of FIGS. 9A and 9B show one, non-limiting example of an ensemble of particles magnetically aligned in a silicone host material. The perspective in FIG. 9A is approximately normal to the host-material layer; the perspective in FIG. 9B is oblique to the host-material layer.

Figure 10:
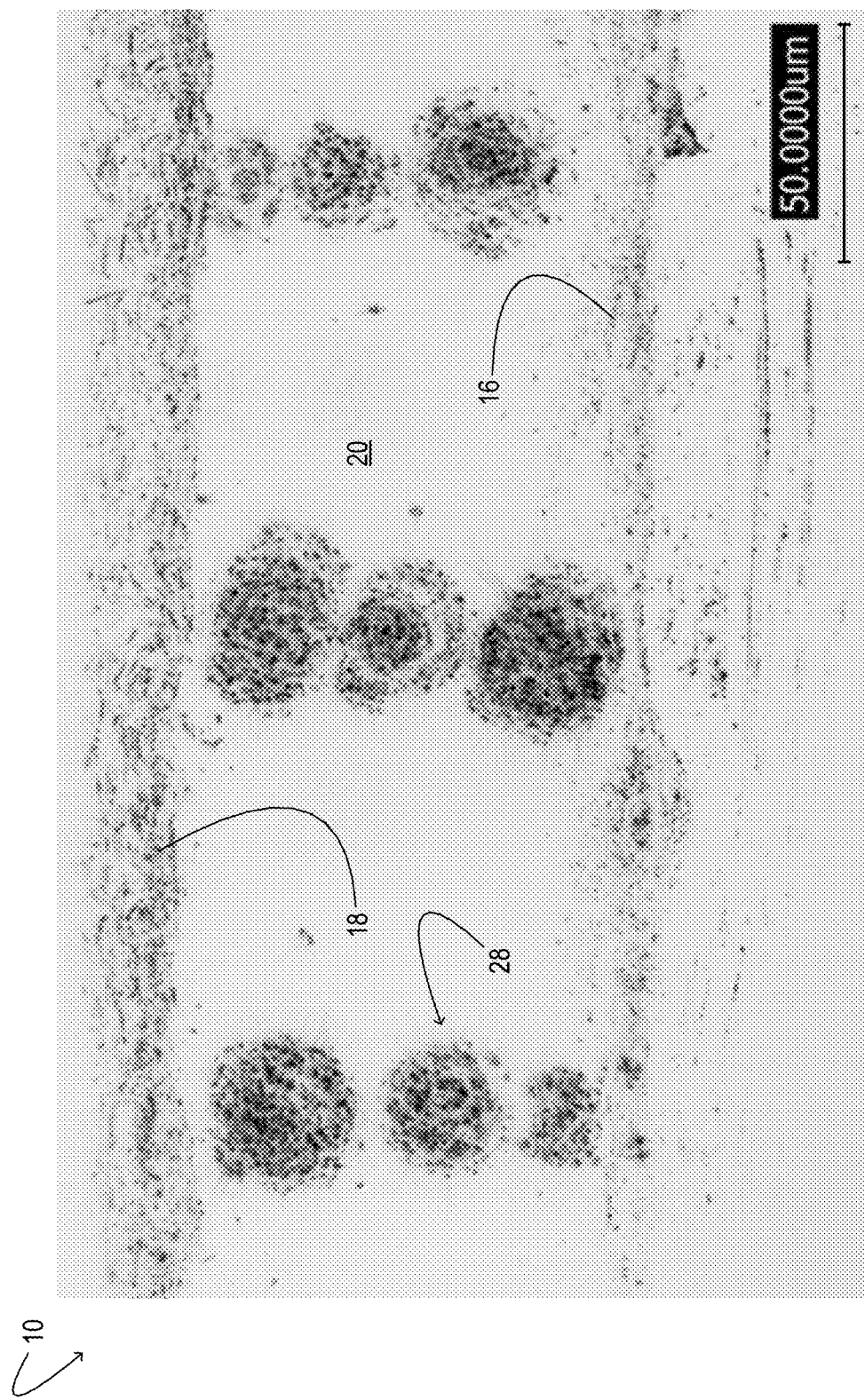
FIG. 10 shows an electron micrograph of a layered structure of an example electronic component.

Returning now to FIG. 7, at 56 the polymer host material may be cured, solidified and/or hardened. Thermal and/or photochemical curing may be employed in some examples. In other examples, a molten thermoplastic host material may be cooled to effect solidification, or volatile solvent may be evaporated, etc. At 58, eutectic gallium indium is deposited onto the surface of the polymer host material. At 60, the eutectic gallium indium first terminal is encapsulated by casting additional uncured polymer host material overtop. FIG. 10 shows an electron micrograph of a final layered structure of electronic component 10, in one non-limiting example.

The structure formed in method 34 allows for a highly conductive second terminal suitable for skin contact, bridged through the ensemble of aligned conductive aligned particles into a eutectic gallium indium first terminal, thereby creating a soft stretchable electronic component for a device. This component may easily conform to the skin and can be utilized as a thin film bioelectrode, measuring electrical signals from the body. In some implementations, as described above, the electrode may further provide pressure-sensitive resistance and/or switching. It may be used, for example, as a switch fully embedded in an elastomeric housing of an electronic device. A switch configured in this manner may be well-protected from environmental conditions, such as condensing moisture, skin-care products, immersion in water, etc.

Another example provides an electronic component comprising a first terminal; a second terminal; a deformable host material arranged between the first terminal and the second terminal; and, aligned magnetically within the host material, an ensemble of particles each having greater electrical conductivity than the host material, the ensemble of particles forming a complete conduction path from the first terminal to the second terminal.

In some implementations, the first terminal may be resiliently deformable. In some implementations, the first terminal may comprise eutectic gallium indium. In some implementations, the first terminal may be fully encapsulated by the host material. In some implementations, the second terminal may be filamentous. In some implementations, the second terminal may form an electrical contact to living human skin. In some implementations, each particle may be about 10 to 50 microns in diameter. In some implementations, the host material may be an electrical insulator. In some implementations, the host material may include a thermosetting polymer. In some implementations, the host material may include silicone. In some implementations, each particle may include a ferromagnetic material and a conductive outer surface. In some implementations, the ensemble of particles may include one or more of silver-coated nickel and silver-coated ferromagnetic oxide particles. In some implementations, the ensemble may form the conduction path upon depression of the host material and may break the conduction path upon release of depression of the host material.

Another example provides a pressure-sensitive electrical switch comprising: a first terminal; a second terminal; a deformable host material arranged between the first terminal and the second terminal; and, aligned within the host material, an ensemble of particles each having greater electrical conductivity than the host material, the ensemble forming a complete conduction path from the first terminal to the second terminal upon depression of the host material and breaking the conduction path upon release of depression of the host material.

In some implementations, the ensemble of particles may be magnetically aligned. In some implementations, the ensemble of particles may be aligned during solidification of the host material, along magnetic field lines arranged between shielded dead zones in which no particles are aligned. In some implementations, forming and breaking the complete conduction path may result from the particles moving in and out of contact with each other with depression and release of depression of the host material.

Another example provides a method to fabricate an electronic component for a wearable device. The method comprises: depositing a filamentous second terminal configured to form an electrical contact against living human skin; depositing a deformable host material over the second terminal; magnetically aligning an ensemble of particles within the host material, each particle having greater electrical conductivity than the host material; and, depositing the first terminal onto the host material, opposite the second terminal, such that the ensemble of particles forms a complete conduction path from the first terminal to the second terminal.

In some implementations, the second terminal may become immobilized in the host material upon solidification of the host material. In some implementations, the second terminal may include conductive nanowires.

It will be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The subject matter of the present disclosure includes all novel and nonobvious combinations and subcombinations of the various processes, systems and configurations, and other features, functions, acts, and/or properties disclosed herein, as well as any and all equivalents thereof.

The invention claimed is:

1. An electronic component, comprising:
   a first terminal;
   a second terminal;
   a deformable host material arranged between the first terminal and the second terminal, the host material fully encapsulating the first terminal; and
   aligned magnetically within the host material, an ensemble of particles each having greater electrical conductivity than the host material, the ensemble of particles forming a complete conduction path from the first terminal to the second terminal.

2. The electronic component of claim 1 wherein the first terminal is resiliently deformable.

3. The electronic component of claim 1 wherein the first terminal comprises eutectic gallium indium.

4. The electronic component of claim 1 wherein the second terminal is filamentous.

5. The electronic component of claim 1 wherein the second terminal forms an electrical contact to living human skin.

6. The electronic component of claim 1 wherein an average particle size is 10 to 50 microns in diameter.

7. The electronic component of claim 1 wherein the host material is an electrical insulator.

8. The electronic component of claim 1 wherein the host material includes a thermosetting polymer.

9. The electronic component of claim 1 wherein the host material includes silicone.

10. The electronic component of claim 1 wherein each particle includes a ferromagnetic material and a conductive outer surface.

11. The electronic component of claim 1 wherein the ensemble of particles includes one or more of silver-coated nickel and silver-coated ferromagnetic oxide particles.

12. The electronic component of claim 1 wherein the ensemble forms the conduction path upon depression of the host material and breaks the conduction path upon release of depression of the host material.

13. A pressure-sensitive electrical switch comprising:
    a first terminal;
    a second terminal;
    a deformable host material arranged between the first terminal and the second terminal, the host material fully encapsulating the first terminal; and
    aligned within the host material, an ensemble of particles each having greater electrical conductivity than the host material, the ensemble being aligned along magnetic field lines arranged between zones in which no particles are aligned, and configured to form a complete conduction path from the first terminal to the second terminal upon depression of the host material and break the conduction path upon release of depression of the host material.

14. The electrical switch of claim 13 wherein the particles are configured to move into and out of contact with depression and release of depression of the host material.

15. An electronic component, comprising:
    a first terminal;
    a second terminal;
    a deformable host material arranged between the first terminal and the second terminal, the host material fully encapsulating the first terminal; and
    aligned magnetically within the host material, an ensemble of particles each having greater electrical conductivity than the host material, the ensemble of particles forming a complete conduction path from the first terminal to the second terminal upon depression of the host material and breaking the conduction path upon release of depression of the host material.

* * * * *